(12) United States Patent
Suzuki

(10) Patent No.: US 7,727,144 B2
(45) Date of Patent: Jun. 1, 2010

(54) ENDOSCOPIC SURGICAL INSTRUMENT

(75) Inventor: Keita Suzuki, Kokubunji (JP)

(73) Assignee: Olympus Corporation (JP)

( * ) Notice: Subject to any disclaimer, the term of this patent is extended or adjusted under 35 U.S.C. 154(b) by 924 days.

(21) Appl. No.: 11/031,549

(22) Filed: Jan. 7, 2005

(65) Prior Publication Data

US 2005/0182292 A1 Aug. 18, 2005

(30) Foreign Application Priority Data

Jan. 16, 2004 (JP) ............................. 2004-008952

(51) Int. Cl.
*A61B 1/00* (2006.01)
(52) U.S. Cl. ................. 600/106; 600/104; 600/118; 600/131; 600/153; 600/154; 600/159
(58) Field of Classification Search ................. 600/104, 600/106, 131, 153–154, 159
See application file for complete search history.

(56) References Cited

U.S. PATENT DOCUMENTS

| | | | | |
|---|---|---|---|---|
| 5,174,276 A | * | 12/1992 | Crockard | 600/104 |
| 5,339,799 A | * | 8/1994 | Kami et al. | 600/117 |
| 5,431,645 A | * | 7/1995 | Smith et al. | 606/1 |
| 6,074,402 A | * | 6/2000 | Peifer et al. | 606/139 |
| 6,569,084 B1 | * | 5/2003 | Mizuno et al. | 600/102 |
| 6,726,675 B1 | * | 4/2004 | Beyar | 604/510 |
| 7,094,202 B2 | * | 8/2006 | Nobis et al. | 600/131 |
| 7,118,582 B1 | * | 10/2006 | Wang et al. | 606/139 |
| 7,169,167 B2 | * | 1/2007 | Chu | 606/205 |
| 7,179,223 B2 | * | 2/2007 | Motoki et al. | 600/131 |
| 2001/0004676 A1 | * | 6/2001 | Ouchi | 600/106 |
| 2001/0016804 A1 | * | 8/2001 | Cunningham et al. | 703/7 |
| 2003/0009085 A1 | * | 1/2003 | Arai et al. | 600/127 |
| 2003/0040737 A1 | * | 2/2003 | Merril et al. | 606/1 |

FOREIGN PATENT DOCUMENTS

JP 2002-330973 11/2002

OTHER PUBLICATIONS

Search Report issued by European Patent Office on May 20, 2005 in connection with corresponding European patent application No. EP 05 00 0501.

* cited by examiner

*Primary Examiner*—Matthew J Kasztejna
(74) *Attorney, Agent, or Firm*—Ostrolenk Faber LLP

(57) ABSTRACT

An endoscopic surgical instrument has an insertion portion to be inserted in a channel of an endoscope, a treatment portion provided at a tip of the insertion portion for treating an objective part and a manipulation portion provided close to a proximal end of the insertion portion. The operator can move the insertion portion forward and backward at least relative to the channel by operating the manipulation portion in a state the endoscopic surgical instrument is inserted in the channel of the endoscope. In this manner, by the manipulation portion, the endoscopic surgical instrument can be operated to move forward and backward relative to the channel. Therefore in case the manipulation portion is located close to a channel entrance (forceps port) of the endoscope, the operator of the endoscope is able to manipulate the endoscopic surgical instrument without assistance from others.

8 Claims, 7 Drawing Sheets

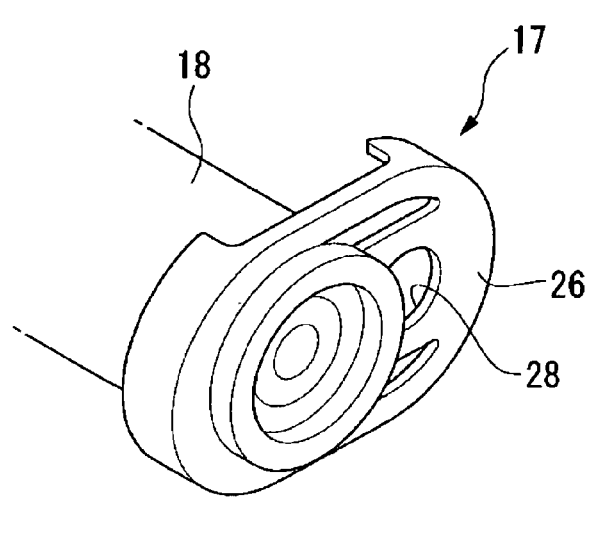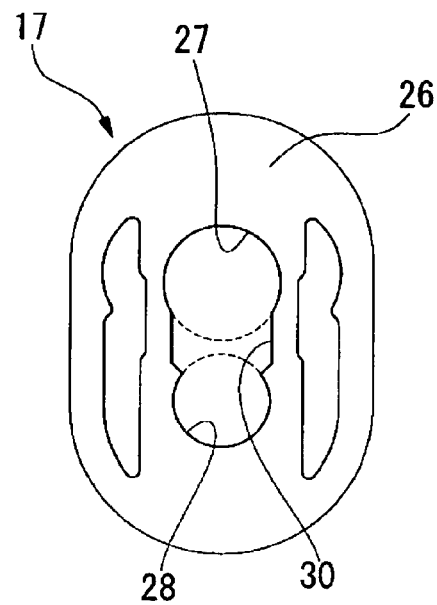
Fig. 3A                Fig. 3B
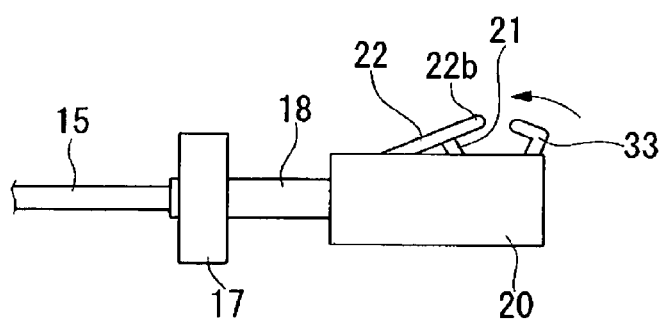
Fig. 4A
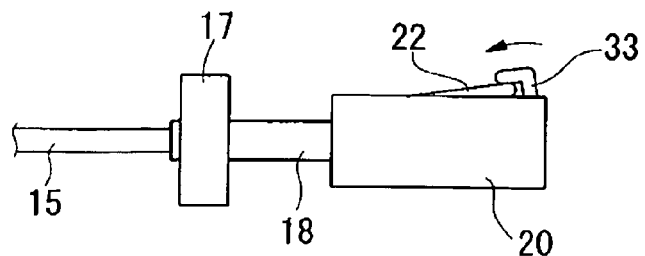
Fig. 4B

ENDOSCOPIC SURGICAL INSTRUMENT

CROSS-REFERENCE TO RELATED APPLICATION

This application is based upon and claims the benefit of priority from the prior Japanese Patent Applications No. 2004-008952, filed on Jan. 16, 2004, the entire contents of which are incorporated herein by reference.

BACKGROUND OF THE INVENTION

1. Field of the Invention

The present invention relates to endoscopic surgical instruments.

2. Description of the Related Art

Conventionally, when conducting medical treatments on specific parts or inspections for diseased parts or the like with an endoscope operated from outside of the body, it is common to carry out various medical treatments by inserting a surgical instrument in a channel of the endoscope.

Such a surgical instrument is longer than an insertion portion of the endoscope, and an instrument manipulation portion for manipulating the surgical instrument is provided at the proximal end of the surgical instrument.

Therefore, when the surgical instrument is inserted in the channel through a forceps port of the channel end, the instrument manipulation portion is left in a distant position from the forceps port. Consequently, an assistant is needed for manipulating the surgical instrument while the operator is manipulating the endoscope.

Auxiliary tools for surgical instruments, by which an endoscope operator can also perform the operation of the surgical instruments, have been proposed for shortening the surgical time. JP-A-2002-330973, FIGS. 22 and 24, disclose one example of such arts.

However, in the conventional surgical instrument, after mounting the auxiliary tool for the surgical-instrument onto an endoscope, the surgical instrument must be inserted and fixed to the auxiliary tool.

BRIEF SUMMARY OF THE INVENTION

An endoscopic surgical instrument of this invention has an insertion portion to be inserted in a channel of an endoscope, a treatment portion provided at a tip of the insertion portion for treating a target, and an instrument manipulation portion provided in the proximal end of the insertion portion. Further in this endoscopic surgical instrument, the instrument manipulation portion is configured so that the operator can move the insertion portion forward and backward relative to the channel by operating the instrument manipulation portion when the endoscopic surgical instrument is inserted in the channel of the endoscope.

Since the operator can advance and retreat the insertion portion relative to the channel with the instrument manipulation portion, if the instrument manipulation portion is provided close to the forceps port (channel opening) of the endoscope, the operator is also able to manipulate the endoscopic surgical instrument.

Preferably, the instrument manipulation portion is fixed close to the forceps port of the endoscope in a releasable manner. In this configuration, the endoscope operator can easily manipulate the instrument manipulation portion to move the endoscope surgical instrument forward and backward relative to the channel.

Preferably, the instrument manipulation portion is configured to be able to rotate the insertion portion and manipulate the treatment portion. In this configuration, various operations of the endoscopic surgical instrument can be carried out near the forceps port of the endoscope.

For example, an endoscopic surgical instrument of this invention comprises an insertion portion to be inserted in a channel of an endoscope, a treatment portion provided at the distal end of the insertion portion, and an instrument manipulation portion provided close to the proximal end of the insertion portion and removably mounted to an endoscope. Further, the instrument manipulation portion integrally has a rotation-manipulation portion for rotating the insertion portion about an axis thereof and an advance/retract-manipulation portion for axially moving the insertion portion forward and backward.

In this endoscopic surgical instrument, by attaching the instrument manipulation portion on the endoscope, the rotation-manipulation portion and advance/retract-manipulation portion become located near the endoscope operator's hand. Thus, the operator can operate the insertion portion received in the endoscope channel for rotations and forward/backward movements thereof with his/her hand.

Preferably, in the endoscopic surgical instrument of the invention, the instrument manipulation portion integrally comprises a treatment manipulation portion for manipulating the treatment portion.

In this endoscopic surgical instrument, the operator can also manipulate the treatment portion provided at the distal end of the insertion portion with his/her hand, together with rotational/advancing-retracting manipulation of the insertion portion.

Preferably, in the endoscopic surgical instrument of this invention, the insertion portion comprises a flexible manipulation tube and a manipulation line member configured to move forward and backward within the manipulation tube. Further, the instrument manipulation portion comprises a mounting mechanism to removably mount the instrument to the forceps port of the endoscope, an outer cylinder on which the mounting mechanism is provided at one end thereof and in which the manipulation tube can be inserted, and a slide portion comprising an inner cylinder. The inner cylinder, connected to the proximal end of the manipulation tube, is able to rotate and move forward/backward relative to the outer cylinder, and is at least partly accommodated inside of the outer cylinder at the one end on which the mounting mechanism is not provided.

In this endoscopic surgical instrument, the operator can rotate the treatment portion about its axis by rotating the slide portion about the axis of the manipulation tube relative to the outer cylinder. Meanwhile, the treatment portion can be advanced/retracted relative to the channel by manipulating the slide portion to move forward and backward relative to the outer cylinder.

Preferably, in the endoscopic surgical instrument that is more fully described further on, the treatment manipulation portion is articulated at the proximal end part of the manipulation line member and the slide portion, and set to be able to move the manipulation line member forward and backward relative to the slide portion.

In this endoscopic surgical instrument, the operator can operate the treatment portion by manipulating the treatment manipulation portion through movement of the manipulation line member forward and backward relative to the slide.

Preferably, the endoscopic surgical instrument further comprises an attaching portion provided at the proximal end of the insertion portion for removably attaching the treatment manipulation portion to the instrument manipulation portion.

In this endoscopic surgical instrument, by attaching the treatment manipulation portion to the instrument manipulation portion, the operator manipulating the endoscope can also operate the endoscopic surgical instrument without assistance from others. Meanwhile, according to the surgical requirements, it is possible that the treatment manipulation portion can selectively be placed away from or near to the instrument manipulation portion. Therefore, an assistant, not the operator, can manipulate the treatment portion as in the conventional cases when it is appropriate.

Preferably, in the endoscopic surgical instrument the mounting mechanism comprises an O-ring provided on the outer cylinder in a manner that enables tight contact to the forceps port.

In this endoscopic surgical instrument, the instrument can closely contact to the endoscope through the O-ring.

Preferably, the endoscopic surgical instrument further comprises a connector for connection to a high-frequency power source to supply high frequency electricity to the treatment portion.

In this endoscopic surgical instrument, a solo operator operating the endoscope can operate the instrument using high frequency electricity.

Preferably, in the endoscopic surgical instrument the outer circumference surface of the manipulation tube is covered with an insulation member in, at least one of, the distal tip portion thereof and the proximal tip portion thereof.

In this endoscopic surgical instrument, since the length of the insertion portion which is insertable into the channel of the endoscope is predetermined, the contact area between the insertion and the channel can be specified beforehand. Therefore, an insulation member for preventing electric leakage caused by the instrument's contact with the channel or the objective portion can be applied only where it is needed. Thus, the resistance caused by the insulation member during the rotational movement is decreased and easiness of operation is increased.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

FIGS. 3A and 3B are views showing one part of the endoscopic surgical instrument according to the first embodiment of the invention;

FIGS. 4A and 4B are side views showing the endoscopic surgical instrument according to the first embodiment of the invention;

DETAILED DESCRIPTION OF THE INVENTION

Preferred embodiments of the invention will be described below with reference to the accompanying drawings.

A first embodiment of the invention is explained below with reference to FIGS. 1 to 4B.

Figure 1:
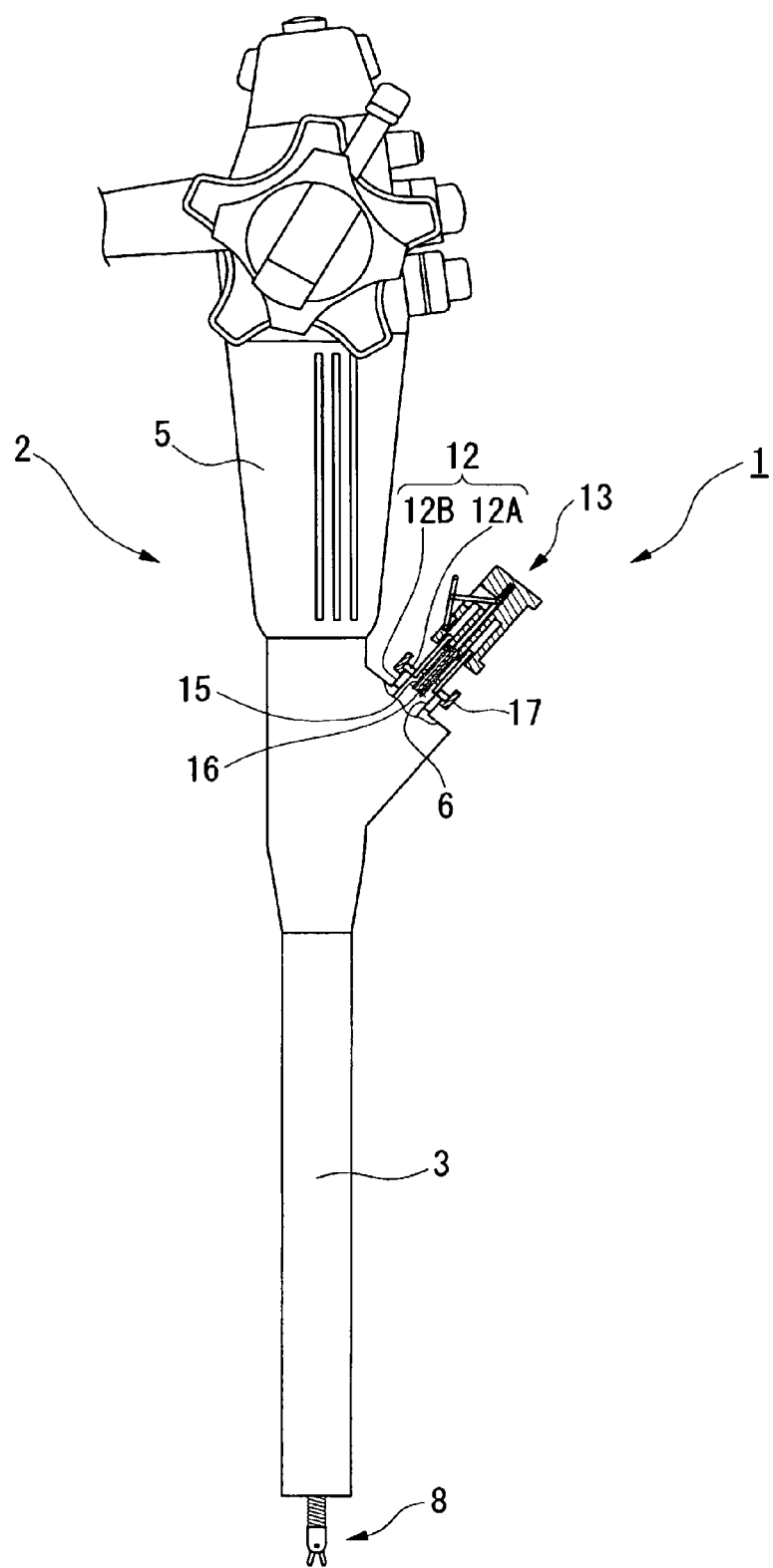
FIG. 1 is a sectional view including a fragmentary section showing a state in which an endscope is mounted to an endoscopic surgical instrument according to a first embodiment of the present invention.

FIG. 1 shows a state in which an endoscope 2 is coupled with an endoscopic surgical instrument 1 according to the first embodiment. The endoscope 2 has an insertion portion 3 and a manipulation portion 5, with a channel 6 formed inside the insertion portion 3.

Figure 2:
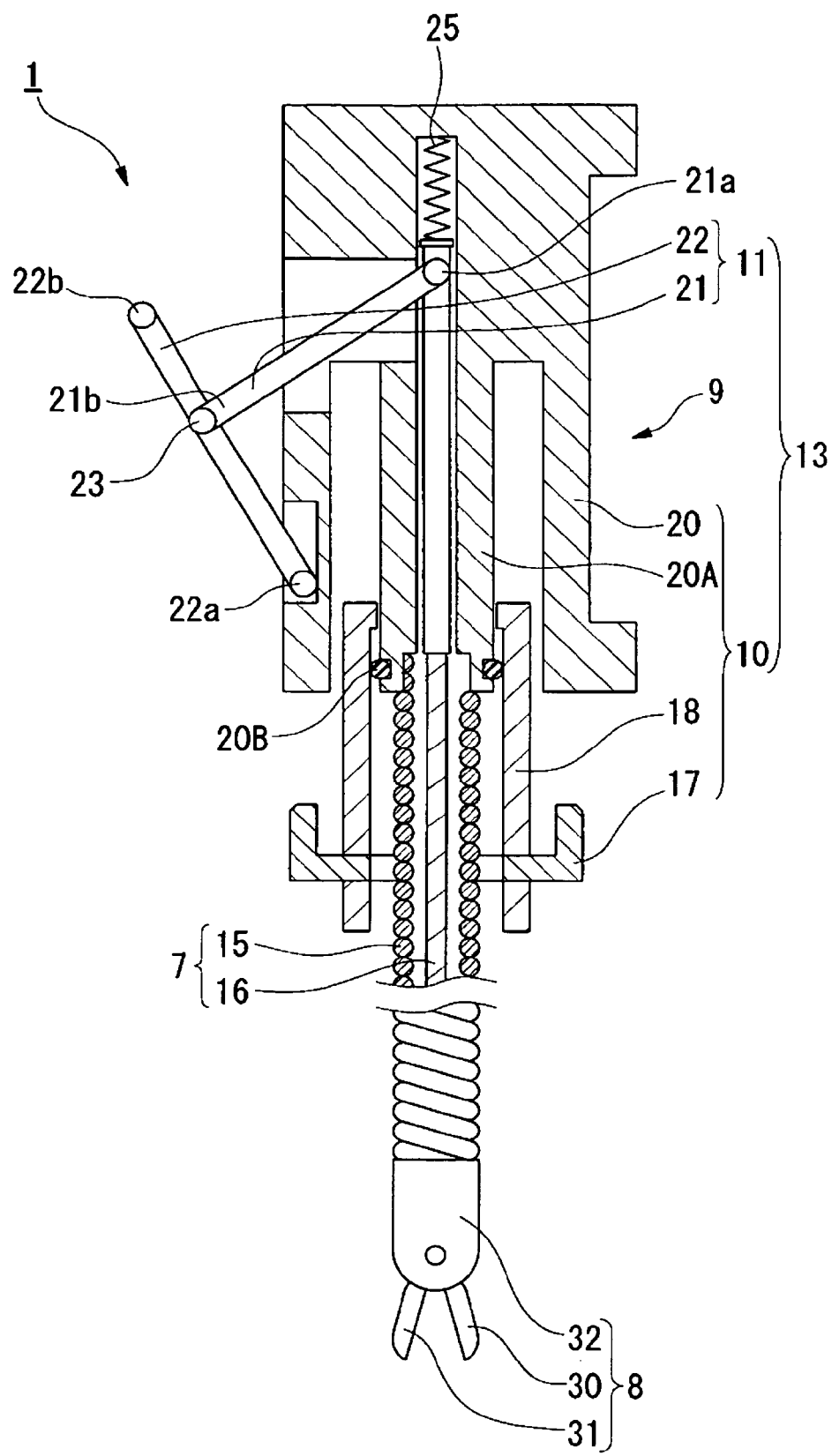
FIG. 2 is a sectional view in a plane including an axis direction representing an endoscopic surgical instrument according to the first embodiment of the invention.

As shown in FIG. 2, the endoscopic surgical instrument 1 has an insertion portion 7 for insertion into the channel 6 of the endoscope 2, a treatment portion 8 connected to a distal end of the insertion portion 7, and an instrument manipulation portion 13 provided close to the proximal end of the insertion portion 7. The instrument manipulation portion 13 further has a rotation-manipulation portion 9 for rotatively manipulating the insertion portion 7 about the axis thereof, an advance/retract-manipulation portion 10 for axially advancing and retracting the insertion portion 7, and a treatment manipulation portion 11 to open and close forceps pieces 30, 31 of the treatment portion 8. This instrument manipulation portion 13 is removably mounted to a forceps port 12 (see FIG. 1) of the endoscope 2.

The insertion portion 7 has a flexible manipulation tube 15 formed of a coiled body, and a manipulation wire 16 (manipulation line member) provided to move forward and backward within the manipulation tube 15.

The advance/retract-manipulation portion 10 has a mounting mechanism 17 which enables it to be removably mounted at the forceps port 12 of the endoscope 2, an outer cylinder 18 one end part of which is fixed to the mounting mechanism 17 and in which the manipulation tube 15 is capable to be inserted, and a slide 20 having an inner cylinder 20A. The inner cylinder 20A is connected to the proximal end of the manipulation tube 15 and arranged, in the proximal end of the outer cylinder 18, for rotation, and advancement and retraction relative to the outer cylinder 18. The diameter of the outer cylinder 18 is suitable for insertion in the channel 6 through the forceps port 12.

An O-ring 20B is provided on an outer circumference surface of the inner cylinder 20A. This configuration allows the inner cylinder 20A to rotate, advance and retract with a proper slide resistance relative to the outer cylinder 18 while keeping airtight contact therewith. Meanwhile, in the inner cylinder 20A, the manipulation wire 16 is such that it is capable of being advanced and retracted.

In this first embodiment, the rotation-manipulation portion 9 is structurally integral with the advance/retract manipulation portion 10.

The treatment manipulation portion 11 serves to move the manipulation wire 16 forward and backward relative to the slide 20. By advancing/retracting the manipulation wire 16, the treatment portion 8 can be opened and closed. The treatment manipulation portion 11 has a first manipulation member 21 and a second manipulation member 22. The first manipulation member 21 is articulated at the base of the manipulation wire 16 at the wire's proximal end 21a. Meanwhile, the second manipulation member has one end 22a articulated at the slide 20 and an intermediate portion having a pivotal point 23 at which the other end 21b of the first manipulation member 21 is articulated and supported. Meanwhile, a spring 25 is provided for connecting the proximal end of the manipulation wire 16 and the slide 20, to bias the manipulation wire 16 toward the distal end thereof.

As shown in FIG. 3A, the mounting mechanism 17 has a plate shaped mount member 26. As shown in FIG. 3B, a first hole 27, a second hole 28, and a communication region 30 bridging both holes are provided in the mount member 26 at the center region thereof, so that the distal end portion of the outer cylinder 18 can move between the first hole 27 and the second hole 28. The first hole 27 has an outer diameter permitting the forceps port end 12A to be inserted therein. The second hole 28 has an outer diameter smaller than the forceps port end 12A but greater than the forceps port main body 12B such that it can be engaged with the forceps port main body 12B (see FIG. 1).

As shown in FIG. 2, the treatment portion 8 has a pair of forceps pieces 30, 31 having bases connected to the distal end of the manipulation wire 16 through a link mechanism (not shown) and a tip cover 32 supporting the pair of forceps pieces 30, 31 in a manner allowing them to open and close. The link mechanism transforms axial manipulation of the manipulation wire 16 into an opening-closing operation of the pair of forceps pieces 30, 31.

The proximal end of the tip cover 32 and the distal end of the manipulation tube 15 are connected, while the proximal end of the link mechanism and the distal end the manipulation wire 16 are connected.

The usage, operation, and effect of the endoscopic surgical instrument 1 according to the present embodiment are described below.

At first, in FIG. 1, the operator inserts the insertion portion 7 of the endoscopic surgical instrument 1 in the channel 6 of the endoscope 2, to thereby fit the endoscopic surgical instrument 1 in the forceps port 12.

In FIG. 2, the tendency of the spring 25 to expand biases the manipulation wire 16 downwards in the figure, toward its distal tip, causing the forceps pieces 30, 31 to open due to the link mechanism. In order to close the forceps pieces 30, 31, the operator holds the second manipulation member 22 near its other end 22b and urges it toward the slide 20, pivoting the manipulation member 22 about the end 22a by grasping. The first manipulation member 21 is then forced to pivot about the pivotal point 23, causing its end 21a is moved upward. The manipulation wire 16 connected with the end 21a at the proximal end thereof, moves upward relative to the manipulation tube 15 causing the link mechanism, which reacts to the axial movement of the manipulation wire 16, to close the forceps pieces 30, 31.

In this state, the operator inserts the insertion portion 7 of the endoscopic surgical instrument into the channel 6 of the endoscope 2 through the forceps port 12 until the mount member 26 contacts with the forceps port 12. Then, the operator engages the first hole 27 of the mount member 26 over the forceps port end 12A and inserts it to the forceps main body 12B, and then moves the mount member 26 toward the second hole 28, thereby fixing the distal tip of the outer cylinder 18 in the forceps port 12. By this operation, the endoscopic surgical instrument 1 becomes mounted on the endoscope 2.

The operator, after moving the distal end of the insertion portion 3 of the endoscope 2 near a treatment point, moves the slide 20 forward relative to the outer cylinder 18 while grasping the other end 22b of the manipulation member 22. Thereupon, both the manipulation tube 15 and the manipulation wire 16 move forward within the outer cylinder 18. Thus, the insertion portion 7 advances within the channel 6.

When the distal end of the treatment portion 8 comes near and further reaches diseased tissue, and if the open and close directions of the pair of forceps pieces 30, 31 are different from grasping directions, the operator rotates the slide 20 about its axis relative to the outer cylinder 18. Thereupon, the inner cylinder 20A rotates about its axis relative to the outer cylinder 18. Because of this, the manipulation tube 15 and manipulation wire 16 can be rotated relative to the channel 6 and adjusted in any a desired rotational orientation relative to the diseased tissue.

To grasp the diseased part, when the operator relaxes the force gripping the second manipulation member 22, the second manipulation member 22 pivots about the end 22a, moving the first manipulation member 21 downward. Then, the spring 25 resorts to pushing the manipulation wire 16 toward the distal end of the insertion portion 3 of the endoscope, which via link mechanism, opens the forceps pieces 30, 31.

When grasping the diseased tissue or part, the operator again grasps the second manipulation member 22 and moves it toward the slide 20 to thereby close the one pair of forceps pieces 30, 31.

In this manner, the diseased part can be grasped by the pair of forceps pieces 30, 31.

As described, in order to maintain the closed state of the one pair of forceps pieces 30, 31, the operator is required to continuously hold the second manipulation member 22, without letting go.

For this reason, as shown in FIG. 4A, it is preferable that an engaging member 33 be articulated at an outer circumference of the slide 20 for engaging with the other end 22b of the second manipulation member 22 when the operator grips the second manipulation member 22 and to place it close to the slide 20.

In this case, as shown in FIG. 4B, when the engaging member 33 is engaged with the second manipulation member 22, the second manipulation member 22 can be fixed to the slide 20. Accordingly, the manipulation wire 16 can be maintained in a position moved toward the distal direction, thereby making it possible to maintain the forceps pieces 30, 31 in the closed state.

According to the endoscopic surgical instrument 1 described above, the operator who is manipulating the endoscope 2, even working solely, is able to perform any of rotational manipulation, or advancing-retracting manipulation or opening-closing manipulation of the treatment portion 8 attached at the distal end of the insertion portion 7 received in the channel of the endoscope 2.

Figure 5:
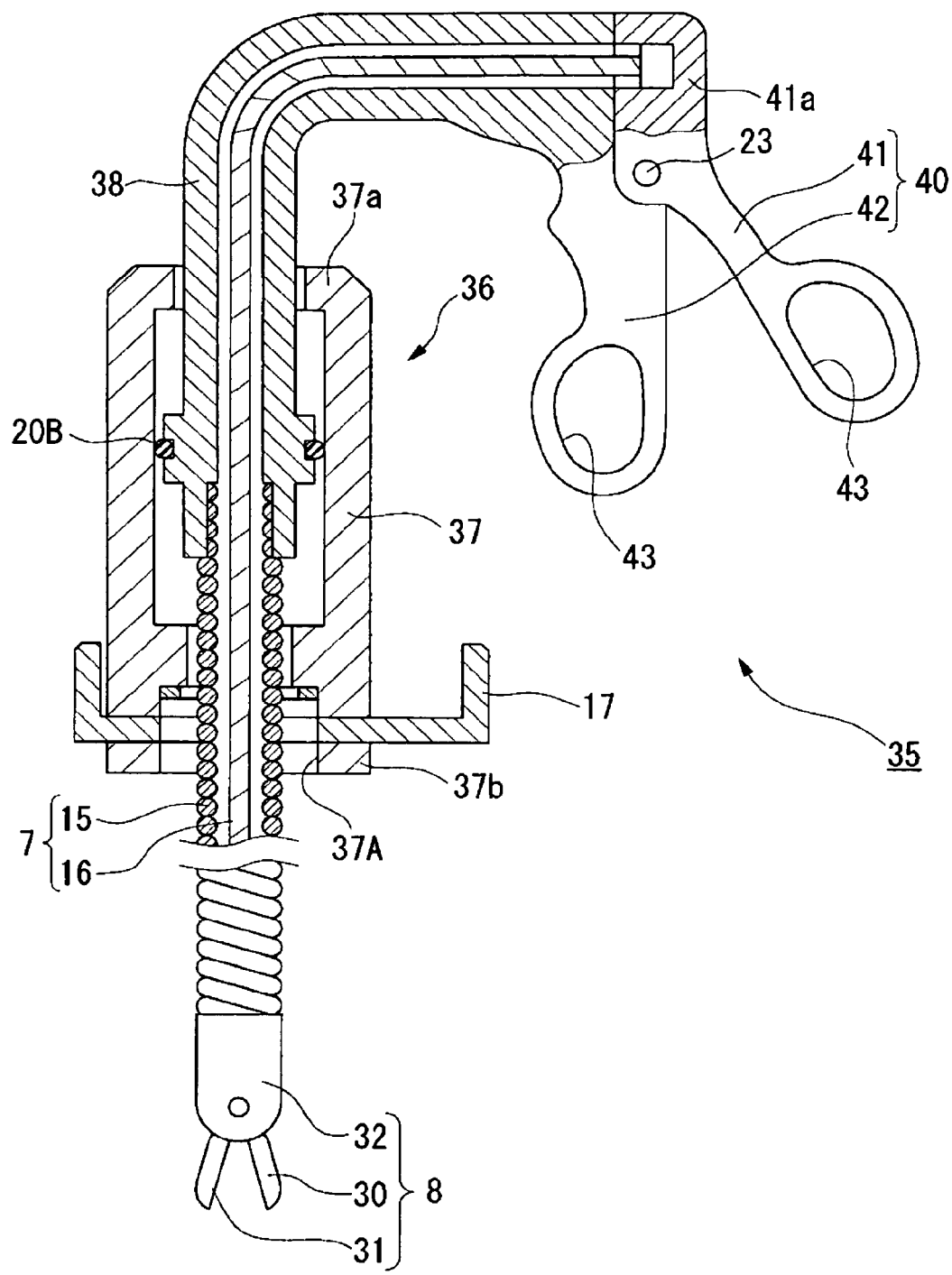
FIG. 5 is a sectional view in a plane including an axis direction representing an endoscopic surgical instrument according to a second embodiment of the invention.

A second embodiment is now explained, referring to FIG. 5.

Note that constituent elements similar to those of the first embodiment are denoted by the same references. As for explanation of those constituent elements, see the first embodiment.

The differences between the second embodiment and the first embodiment lie in that the advance/retract-manipulation portion 36 of the endoscopic surgical instrument 35 in the second embodiment has an outer cylinder 37 and an inner cylinder 38 protruding outward from the base 37a of the outer cylinder 37, and in that the treatment manipulation portion 40 can move the manipulation wire 16 forward and backward relative to the inner cylinder 38. The treatment manipulation portion 40 has a first manipulation member 41 having one end 41a connected with the proximal end of the manipulation wire 16, a second manipulation member 42 connected with the proximal end of the inner cylinder 38 and a pivotal point 23 rotatably supporting the first manipulation member 41 relative to the second manipulation member 42.

The first manipulation member 41 and the second manipulation member 42 are provided with respective handles 43 at their proximal ends so that the operator can pivot the first manipulation member 41 about the pivotal point 23 relative to the second manipulation member 42 with his/her fingers in the handles 43.

The outer cylinder 37 is connected, at a side close to the distal end, with a mounting mechanism 17 removably mounted to the forceps port 12. Meanwhile, the outer cylinder 37 has a distal end 37b formed with a recess 37A having an inner diameter engagable with the forceps port end 12A. The mounting mechanism 17 can be manipulated when the forceps port end 12A and the recess 37A are fitted with each other.

The inner cylinder 38 has a distal end connected to a base of the manipulation tube 15. The inner cylinder 38 is allowed to rotate and advance/retract within the outer cylinder 37 through an O-ring 20B arranged on the outer circumference surface of the inner cylinder 38, in the proximal end side of the outer cylinder 37.

Meanwhile, the inner cylinder 38 is flexible and bendable at least at its proximal end side, and the manipulation wire 16 is provided within the inner cylinder 38 such that it can be moved forward and backward.

The second embodiment is also structured with the rotation-manipulation portion integral with the advance/retract-manipulation portion 36.

The usage, operation, and effects of the endoscopic surgical instrument 35 according to the second embodiment are described below.

In the initial state of the second embodiment, the pair of forceps pieces 30, 31 are in their closed state. The operator inserts the insertion portion 7 directly into the channel 6 of the endoscope, to thereby attach the endoscopic surgical instrument 35 in the forceps port 12 similarly to the first embodiment.

The operator moves the distal end of the inserting portion 3 near a diseased part or tissue and then moves the inner cylinder 38 forward relative to the outer cylinder 37, thus moving both the manipulation tube 15 and the manipulation wire 16 forward within the outer cylinder 37 and hence within the channel 6.

When the opening/closing state of the forceps pieces 30, 31 is different from the state when the treatment portion 8 tip has reached the diseased part, the operator rotates the inner cylinder 38 about its axis relative to the outer cylinder 37. At this time, because the manipulation tube 15 and the manipulation wire 16 rotate relative to the channel 6, the treatment portion 8 can be adjusted to the desired opening and closing position.

Then, the operator places his/her fingers in the handles 43 of the first manipulation member 41 and second manipulation member 42 and moves them closer to each other.

At this time, the first manipulation member 41 rotates about the pivotal point 23 thereby moving the manipulation wire 16 toward the proximal direction relative to the manipulation tube 15. Thus, the link mechanism is operated by axial movement of the manipulation wire 16, thereby opening the one pair of forceps pieces 30, 31.

To grasp the tissue, the operator again moves the first manipulating member 41 and second manipulating member 42 away from each other, to rotate the first manipulation member 41 about the pivotal point 23 relative to the second manipulating member 42 thereby moving the manipulation wire 16 toward the distal direction relative to the manipulation tube 15. By this manipulation, the forceps pieces 30, 31 are closed.

The endoscopic surgical instrument 35 obtains an operation and effects similar to those of the first embodiment. Particularly, manipulation is easier when force is required in a direction to open the one pair of forceps pieces 30, 31. Namely, during manipulation of the treatment manipulation portion 40, manipulation is possible by putting the fingers in the handles 43, thus making it possible to carry out an opening-closing operation of the one pair of forceps pieces 30, 31 more easily.

Figure 6A:
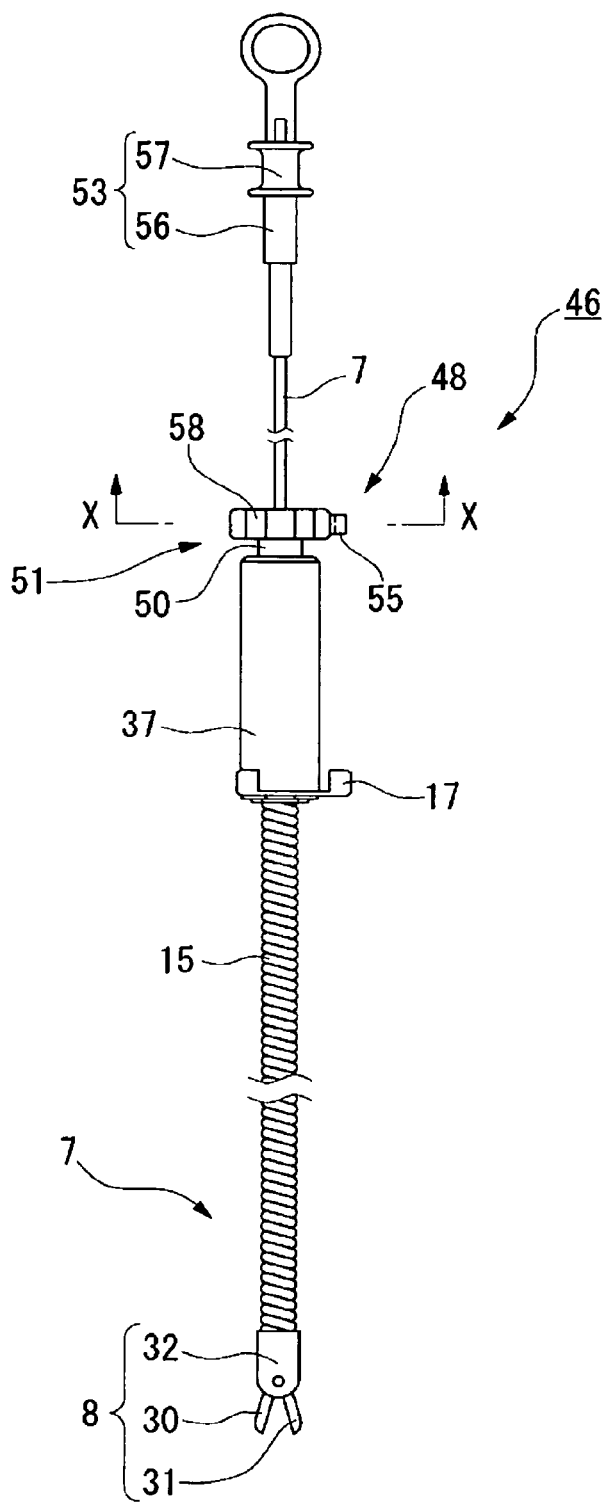
FIGS. 6A and 6B are side views showing an endoscopic surgical instrument according to a third embodiment of the invention.
Figure 6B:
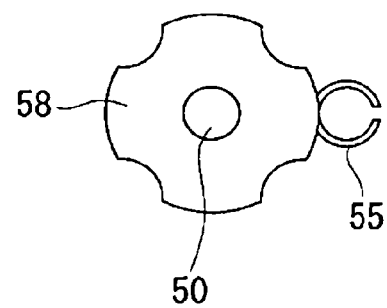

Now a third embodiment is explained while referring to FIGS. 6A and 6B.

Note that constituent elements similar to those of the foregoing embodiments are denoted with the same references. As for explanation of those constituent elements, see the above first and second embodiments. The differences between the third embodiment and the second embodiment lie in that the advance/retract-manipulation portion 48 of the endoscopic surgical instrument 46 in the third embodiment has a slide 51 and wherein the slide 51 has an outer cylinder 37 and an inner cylinder 50 provided for rotation, and advancement and retraction relative to the outer cylinder 37 at the proximal side of the outer cylinder 37. Also, the treatment manipulation portion 53, connected to the proximal end of the insertion portion 7 for operating the treatment portion 8, has a removable attaching portion 55. Further, the operation tube 15 is bonded to the inner cylinder 50 through the outer cylinder 37 and the treatment manipulation portion 53 is directly provided at the proximal end of the manipulation tube 15.

The treatment manipulation portion 53 has a manipulation portion main body 56 connected to the base of the manipulation tube 15, and an operation part 57 connected to the distal end of the manipulation wire 16 in a manner capable of advancing and retracting relative to the manipulation portion main body 56. The slide 51 at its proximal end is connected with a flange 58 capable of advancing/retracting, rotating and holding the inner cylinder 50.

The holding part 55 is arranged in a side surface of the flange 58 and formed as a C-shaped elastic member capable of receiving and holding the manipulation portion main body 56 therein. Usually, the manipulation portion main body 56 is inserted in the holding part 55 and held there.

The operation, and effects of the endoscopic surgical instrument 46 according to the present embodiment are described below.

At first, the operator attaches the endoscopic surgical instrument 46 to the forceps port 12 similarly to the second embodiment.

The operator moves the distal end of the insert ion portion 3 near a diseased part, and then grasps the flange 58 and thereby moves inner cylinder 50 forward relative to the outer cylinder 37. At this time, both the treatment manipulation portion 53 and the manipulation wire 16 move forward within the outer cylinder 37, thus advancing within the channel 6.

When the opening and closing position of the forceps pieces 30, 31 is different from the desired position when the treatment portion 8 tip has reached the diseased part, the operator rotates the flange 58 about its axis relative to the outer cylinder 37. At this time, the inner cylinder 50 rotates relative to the outer cylinder 37, to rotate the manipulation tube 15 and manipulation wire 16 relative to the channel 6. Thus, the treatment portion 8 is adjusted into the desired position.

Then, the operator moves the operation part 57 toward the distal direction relative to the manipulation portion main body 56, to advance the manipulation wire 16 toward the distal direction relative to the manipulation portion tube 15.

Thus, the link mechanism is operated by axial movement of the manipulation wire 16, thereby opening the pair of forceps pieces 30, 31.

To effect grasping, the operating part 57 is moved toward the proximal direction of the manipulation portion main body 56 to thereby move the manipulation wire 16 toward the proximal direction relatively to the manipulation portion tube 15. Due to this, the forceps pieces 30, 31 are closed.

The endoscopic surgical instrument of the third embodiment also obtains operation/effects similar to those of the foregoing embodiment.

Here too, by placing the manipulation portion main body 56 to the holding part 55 of the flange 58, the operator manipulating the endoscope 2, even working solely, is allowable to manipulate the treatment portion 8.

On the other hand, by positioning the manipulation portion main body 56 away from the holding part 55 when so required, the treatment portion 8 can be manipulated by an assistant, rather than by the operator.

Figure 7:
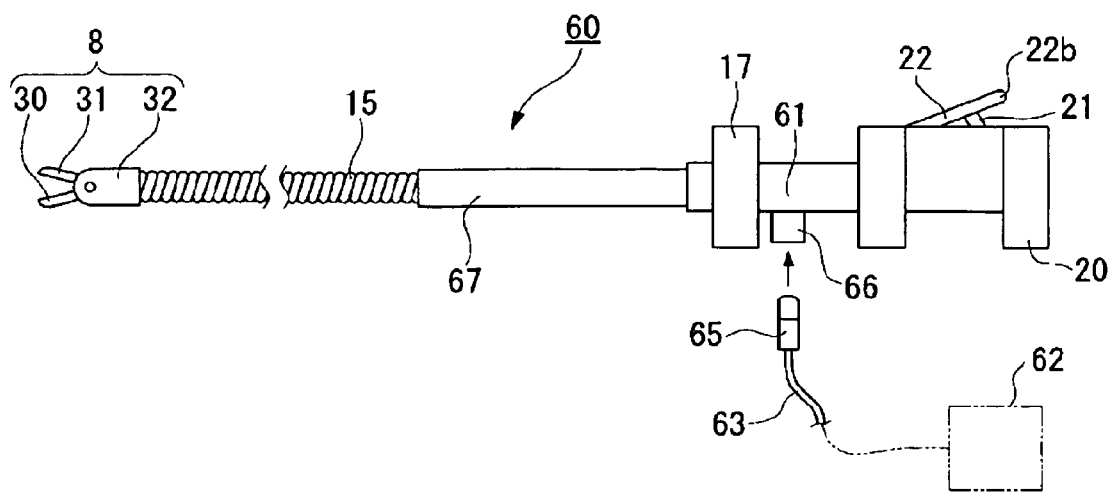
FIG. 7 is a side view showing an endoscopic surgical instrument according to a fourth embodiment of the invention.

Now a fourth embodiment is explained while referring to FIG. 7.

Note that those constituent elements that are similar to those of the foregoing embodiment are denoted with the same references. As for explanation of those constituent elements, see the first, second and third embodiments.

The difference between the fourth embodiment and the first embodiment lies in that an instrument-side connector (connection) 66 is provided on a side surface of the outer cylinder 61 of the endoscopic surgical instrument 60 in the fourth embodiment. The connector 66 is to be connected with a power-source-side connector 65 connected to a distal end of a line 63 extending from a high-frequency power source 62 capable of supplying high-frequency power to the treatment portion 8. The instrument-side connector 66 is provided with an insertion hole in which the power-source-side connector 65 can be fitted.

The manipulation tube 15 has a proximal side of an outer surface covered with an insulation tube (insulation member) 67 preventing contact with the channel 6. Meanwhile, the instrument-side connector 66 is provided to be able to contact to the manipulation wire 16.

This endoscopic surgical instrument 60 obtains an operation and effects similar to those of the other embodiment. Further, by attaching it to the forceps port 12, a high-frequency wave can be supplied in a stable state.

The technical scope of the invention is not limited to the foregoing embodiments but can be modified in various ways which are apparent to those of skill in the art.

Figure 8:
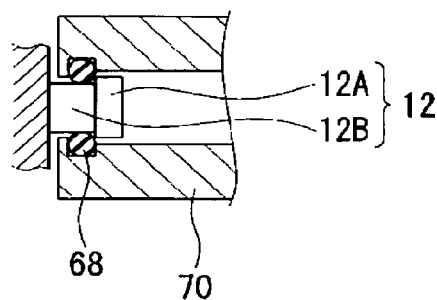
FIG. 8 is a sectional view showing one part of an endoscopic surgical instrument according to another embodiment of the invention.

For example, although the foregoing first embodiment was provided with a mount member 26 formed with a mounting mechanism in a plate form, an O-ring (attaching mechanism) 68 may be provided which is closely fitted with the forceps port main body 12B and formed smaller in diameter than the forceps port end 12A, as shown in FIG. 8. In this case, the outer cylinder 70 and the forceps port 12 can be closely fitted and both can be arranged for relative rotation.

Figure 9A:
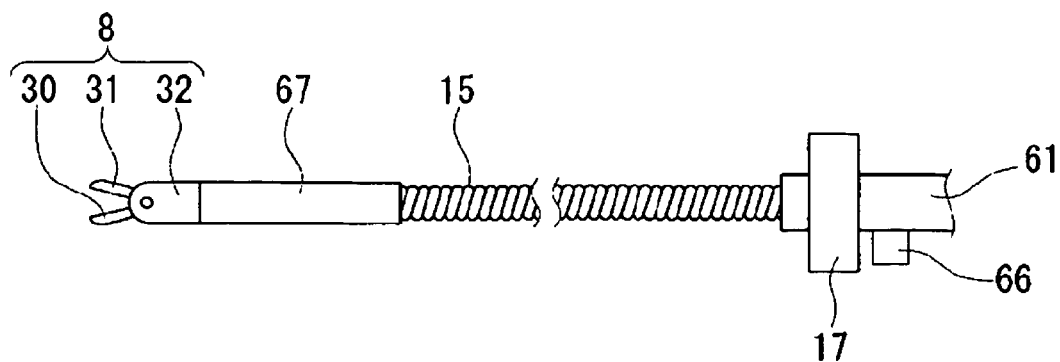
FIGS. 9A and 9B are side views showing an endoscopic surgical instrument according to another embodiment of the invention.
Figure 9B:
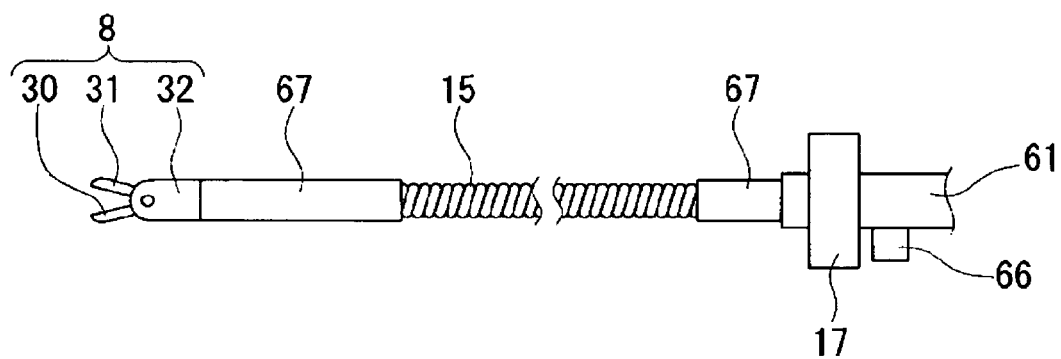

Further, the insulation tube 67 covering the manipulation tube 15 of the endoscopic surgical instrument 60 of the fourth embodiment may cover the distal side of outer surface of the manipulation tube 15 as shown in FIG. 9A or cover both distal and proximal sides of outer surfaces of the manipulation tube 15 as shown in FIG. 9B.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscopic surgical instrument insertable into and removable from a forceps port of a channel of an endoscope, the endoscopic surgical instrument comprising:

an insertion portion at least partially insertable in the channel of the endoscope and comprising as one unit a manipulation tube including a tip at a distal portion thereof, a treatment portion provided at the distal tip of the manipulation tube and fixed thereto, a manipulation wire portion positioned within the manipulation tube and connected to the treatment portion for operating the treatment portion through forward and backward movement of the manipulation wire portion relative to the manipulation tube, and a treatment manipulation portion for operating the treatment portion by moving the manipulation wire portion forward and backward relative to the manipulation tube; and an instrument manipulation portion positioned proximal of the manipulation tube and fixed thereto, the instrument manipulation portion configured to rotate the insertion portion as one unit around in the channel of the endoscope and to cause the forward and backward movement of the insertion portion as one unit relative to the channel of the endoscope, the instrument manipulation portion comprising a mounting mechanism for removably mounting the instrument manipulation portion on the endoscope.

2. The endoscopic surgical instrument according to claim 1, wherein the treatment manipulation portion is integrally provided with the instrument manipulation portion.

3. The endoscopic surgical instrument according to claim 1, further including:

an outer cylinder to which the mounting mechanism is connected at one end portion thereof and, in which the manipulation tube is inserted; and a slide connected to a proximal end of the manipulation tube and comprising an inner cylinder connected to the proximal end of the manipulation tube, the inner cylinder being at least partly accommodated inside of the outer cylinder at an end which the mounting mechanism is not provided, and being able to rotate and move forward/backward relative to the outer cylinder.

4. The endoscopic surgical instrument according to claim 3, wherein a treatment manipulation portion is able to move the manipulation wire forward and backward relative to the slide, and is articulated at a proximal portion of the manipulation wire and the slide.

5. The endoscopic surgical instrument according to claim 3, wherein the mounting mechanism includes an O-ring provided on the outer cylinder, in a closely fitting slot of the forceps port.

6. The endoscopic surgical instrument according to claim 1, wherein the instrument manipulation portion is provided with a connector for connection to a high-frequency power source capable of supplying high-frequency energy to the treatment portion.

7. The endoscopic surgical instrument according to claim 6, wherein the outer circumference surface of the manipulation tube comprising an insulation member, the insulation member positioned to cover at least one of the distal tip portion and the proximal tip portion of the manipulation tube.

8. In combination, the endoscopic surgical instrument according to claim 1 and the endoscope.

* * * * *